United States Patent
Miyakoshi et al.

(10) Patent No.: US 9,387,278 B2
(45) Date of Patent: Jul. 12, 2016

(54) MEDICAL DEVICE OR INSTRUMENT HAVING POROUS STRUCTURE

(75) Inventors: Takayuki Miyakoshi, Suwa (JP); Toshimasa Tokuno, Suwa (JP); Tomoya Kitano, Suwa (JP); Kazutaka Yoshino, Takarazuka (JP); Yasuo Seki, Takarazuka (JP)

(73) Assignees: Sun Medical Technology Research Corp., Nagano (JP); Hi-Lex Corporation, Hyogo (JP)

( * ) Notice: Subject to any disclaimer, the term of this patent is extended or adjusted under 35 U.S.C. 154(b) by 272 days.

(21) Appl. No.: 13/126,451

(22) PCT Filed: Sep. 24, 2009

(86) PCT No.: PCT/JP2009/004826
§ 371 (c)(1),
(2), (4) Date: Jul. 5, 2011

(87) PCT Pub. No.: WO2010/050114
PCT Pub. Date: May 6, 2010

(65) Prior Publication Data
US 2011/0313237 A1 Dec. 22, 2011

(30) Foreign Application Priority Data
Oct. 28, 2008 (JP) .................................. 2008-277114

(51) Int. Cl.
*A61M 1/10* (2006.01)
*A61L 29/14* (2006.01)
(Continued)

(52) U.S. Cl.
CPC .............. *A61L 29/146* (2013.01); *A61M 1/122* (2014.02); *A61M 1/3653* (2013.01); *A61M 1/3659* (2014.02)

(58) Field of Classification Search
CPC .................................. A61F 2/022; A61F 2/02
USPC .......................................................... 600/16
See application file for complete search history.

(56) References Cited

U.S. PATENT DOCUMENTS

| | | | | |
|---|---|---|---|---|
| 4,086,665 | A | * | 5/1978 | Poirier .......................... 623/1.44 |
| 4,405,319 | A | * | 9/1983 | Cosentino ..................... 604/175 |

(Continued)

FOREIGN PATENT DOCUMENTS

| | | |
|---|---|---|
| EP | 0 174 802 A2 | 3/1986 |
| JP | 61-360 A | 1/1986 |

(Continued)

OTHER PUBLICATIONS

Japanese Office Action mailed Dec. 16, 2012, in corresponding Japanese Application No. 2010-002934, filed Jan. 8, 2010, 4 pages.

(Continued)

*Primary Examiner* — Christopher D Koharski
*Assistant Examiner* — Michael D Abreu
(74) *Attorney, Agent, or Firm* — Christensen O'Connor Johnson Kindness PLLC

(57) ABSTRACT

The present invention relates to an inflow cannula for blood circulatory assist devices, having a robust structure and possessing a thrombus anchoring effect. Furthermore, the inflow cannula for blood circulatory assist devices does not deform or exhibit loss of dimensional accuracy during the manufacture process. These features are achieved by a porous structure formed of one or more linear elements or of a porous shaped article.

17 Claims, 12 Drawing Sheets

(51) Int. Cl.
  *A61M 1/36* (2006.01)
  *A61M 1/12* (2006.01)

(56) References Cited

U.S. PATENT DOCUMENTS

| | | | |
|---|---|---|---|
| 4,496,349 A * | 1/1985 | Cosentino | 604/175 |
| 4,654,033 A | 3/1987 | Lapeyre | |
| 4,822,341 A | 4/1989 | Colone | |
| 4,822,361 A * | 4/1989 | Okita et al. | 623/23.71 |
| 5,449,342 A | 9/1995 | Hirose | |
| 6,050,975 A | 4/2000 | Poirier | |
| 2003/0050528 A1* | 3/2003 | Shannon et al. | 600/16 |
| 2003/0083678 A1 | 5/2003 | Herweck | |
| 2004/0059178 A1 | 3/2004 | McCarthy | |
| 2004/0088038 A1* | 5/2004 | Dehnad | A61F 2/91 623/1.15 |
| 2004/0204686 A1 | 10/2004 | Porter | |
| 2007/0299297 A1 | 12/2007 | Jarvik | |

FOREIGN PATENT DOCUMENTS

| | | |
|---|---|---|
| JP | 62500006 U | 6/1987 |
| JP | 2-86553 U | 7/1990 |
| JP | 4-193181 A | 7/1992 |
| JP | 5-200110 A | 8/1993 |
| JP | 10-508212 A | 8/1998 |
| JP | 2002-510232 A | 4/2002 |
| JP | 2004-97268 A | 4/2004 |
| JP | 2006-520621 A | 9/2006 |
| JP | 2007-524443 A | 8/2007 |
| JP | 2008-511414 A | 4/2008 |
| JP | 2008-279188 A | 11/2008 |
| JP | 2009-112577 A | 5/2009 |
| JP | 2010-104428 A | 5/2010 |
| WO | 86/04509 A1 | 8/1986 |
| WO | 95/20984 A2 | 8/1995 |
| WO | 2004/091432 A2 | 10/2004 |
| WO | 2007/089500 A2 | 8/2007 |

OTHER PUBLICATIONS

Harasaki, H., et al., "Powdered Metal Surface for Blood Pump," Transactions—American Society for Artificial Internal Organs 25(1):225-231, Apr. 1979.

Japanese Official Action mailed Feb. 12, 2013, issued in corresponding Japanese Application No. 2010-158037, filed Sep. 24, 2009, 4 pages.

Extended European Search Report mailed Mar. 6, 2013, issued in corresponding Application No. EP 09 82 3230.9, filed Sep. 24, 2009, 10 pages.

\* cited by examiner (A)

(B)

(A)

(B)

(A)

(B)

MEDICAL DEVICE OR INSTRUMENT HAVING POROUS STRUCTURE

TECHNICAL FIELD

The present invention relates to a medical device or instrument having a porous structure with a thrombus anchoring function, the medical device or instrument allowing long-term indwelling use in vivo, and also relates to a method of manufacturing the medical device or instrument, and to use thereof.

BACKGROUND ART

In recent years, whole-body circulation has come to be assisted through the use of an artificial heart or the like if cardiac function is compromised owing to conditions such as heart failure or the like. Ventricular assist devices can temporarily replace the cardiac function, lost on account of, for instance, heart disease, external injury, or heart attack, until recovery of the cardiac function or while waiting for a heart transplant, or can replace cardiac function permanently, thereby keeping the patient alive, all of which underscore the importance of such devices.

In particular, it is well known that left ventricular assist devices are extremely effective for ameliorating symptoms in patients of congestive heart failure. Left ventricular assist devices have been developed as a last-resort therapy for patients of severe congestive heart failure, for instance, patients who cannot undergo a heart transplant either temporarily or permanently, and who require long-term circulatory support. Left ventricular assist devices can assume the function of the left ventricle, namely, pumping into the whole body the blood that has taken up oxygen in the lungs. A left ventricular assist device is attached to the heart and blood vessels of the patient, and can be removed once the natural heart has recovered.

Ordinary ventricular assist devices comprise mainly, for instance, devices or instruments such as a blood pump, a controller, a battery, a cannula, an outflow graft and the like. The foregoing are surgically implanted in the thoracic cavity of the patient. To do so, a cannula is inserted into a ventricle (left or right ventricle) or an atrium (left or right atrium), blood is drained, blood flow is started by a blood pump, and blood is returned to the aorta via an outflow graft. The above procedure allows securing blood circulation in a patient with impaired cardiac function.

Artificial hearts and ventricular assist devices dwell in the body for long periods of time, and hence the devices or instruments that make up the foregoing must possess such mechanical strength as allows them to retain a stable structure when implanted in vivo for long periods of time. Should part of such device or instrument be damaged and release, as a result, fragments or the like into the bloodstream, an embolism may occur. Therefore, mechanical strength must be rigorously guaranteed.

In addition to the above-described mechanical strength issue, long-term use of an artificial heart or a ventricular assist device is complicated by the serious problem of circulatory deficit caused by thrombi. For instance, a thrombus forming and growing in the blood pump may occlude blood flow passages or cause the pump to stop. Even if the thrombus is very small, detachment thereof might occlude a peripheral blood vessel, thereby posing significant danger to life. For the purpose of avoiding such problem, the devices, instruments and so forth comprised in artificial hearts and ventricular assist devices have used conventionally antithrombogenic materials, or materials the surface of which is provided with some antithrombogenic means.

However, even if such materials are used in the devices or instruments that make up an artificial heart or a ventricular assist device, thrombi tend to form readily, for example, on the outer peripheral face of a cannula which is inserted into the heart, i.e., on the outer peripheral face of an inflow cannula. This thrombus formation tendency on the outer peripheral face of an inflow cannula arises from the blood pooling in the gap which forms between the outer peripheral face of the inflow cannula and the inner wall of the own heart since the inflow cannula is disposed so as to protrude into a ventricle (left or right ventricle) or an atrium (left or right atrium), and from the blood's property of being prone to coagulate at slow flow sites. In actuality, it has been found that insertion into the heart of a conventionally used inflow cannula made of titanium and having a smooth surface, i.e., having the surface smoothed by polishing or the like, may result in formation of thrombi on the surface of the cannula within a short period of time. If a thrombus detaches in the left ventricle or the like, it enters the bloodstream at once and is carried into the body, where it may cause an infarction in a thin blood vessel. This may give rise to conditions, such as cerebral infarction or renal infarction, that have a devastating impact on the patient. The same problem besets devices or instruments other than the inflow cannula, such as blood pumps (in particular, the pump inner surface that is in contact with the blood), connectors or the like that make up as well an artificial heart or a ventricular assist device, and which are indwelling at sites where blood pools easily.

To deal with the above problem, the blood-contacting surface of devices or instruments that make up a ventricular assist device is provided with a textured surface, i.e., a surface formed with irregularities or pores, or alternatively, a structure having a textured surface is separately arranged and fixed onto the blood-contacting surface of the above devices or instruments, as an attempt at anchoring thrombi stably by way of the irregularities and/or pores of the textured surface, in particular, by way of the voids formed in the pores. Such thrombus anchoring should allow preventing thrombi from getting into the blood, while allowing endothelial cells to be adhered onto the anchored thrombi, depending on the sites at which the above textured surface is provided. As is known, endothelial cells exhibit very high antithrombogenicity. Ultimately, covering with endothelial cells the entire blood-contacting surface in the ventricular assist device would therefore be ideal in terms of preventing thrombus formation.

As an example of a ventricular assist device using such a textured surface, H. Harasaki et al. (H. Harasaki et al. Powdered Metal Surface for Blood pump. Trans Am Soc Artif Intern Organs, 1979; 25; 225-230) discloses a pulsatile blood pump, the surface of which is coated with sintered titanium alloy spheres. In the blood pump by Harasaki et al., multiple titanium alloy spheres are sintered onto the surface of the blood pump, to form thereby, on the blood pump, a textured surface comprising the sintered titanium alloy spheres. It is observed therein that the best anchoring effect is achieved when using titanium alloy spheres having a particle size distribution lying within 75 to 150 micrometer. In this regard, it has been found that the pores, which are formed between the spheres when using multiple spheres having such a particle size range, have an opening surface area of about not less than $0.22 \times 10^{-3}$ mm$^2$ (if converted to equivalent circular diameter, this opening surface area yields a diameter of about 17 micrometer), when performing calculations under the assumption that all the spheres are arranged regularly, and the pores formed between spheres are smallest when spheres having the smallest particle size (75 micrometer) are arrayed in a dense packing.

U.S. Pat. No. 6,050,975 discloses a blood pump using a textured surface in some components. Here also, as is the case in H. Harasaki et al., the textured surface used is a sintered titanium sphere layer formed by sintering titanium spheres onto the surface of the component.

US2007/0299297 A1 discloses an axial flow pump of a type in which the blood pump is inserted directly into the left ventricle, such that a structure having a sintered titanium microsphere layer is arranged on the outer peripheral face of the blood pump that comes into contact with blood. In this case as well, the sintered titanium microsphere layer plays the role of a textured surface. In the blood pump disclosed in US2007/0299297 A1, however, the titanium microspheres are sintered onto a member called a "wall shell", independently from the blood pump, after which the wall shell having the sintered titanium microsphere layer is fitted onto the outer peripheral face of the blood pump.

As described above, covering the entire blood-contacting surface of a ventricular assist device with endothelial cells, by way of a textured surface, would be ideal in terms of anti-thrombogenicity. However, the number of cell divisions that endothelial cells can undergo is limited in practice, and hence endothelial cells do not reach up to sites that are removed at a distance from living tissue. Therefore, covering the entire blood-contacting surface in the ventricular assist device with endothelial cells is next to impossible. Thus, even if part of the blood-contacting surface were covered with endothelial cells when using a textured surface over the entire blood-contacting surface, there would still remain other sites uncovered with the endothelial cells. Should germs get mixed with the blood, the textured surface sites not covered with endothelial cells will become breeding grounds for germs within the textured surface. Once germs have become established there, the affected sites are very unlikely to be reverted to a normal state. Removing the germs with antibiotics or the like is difficult, and sepsis may set in over time.

In practical terms, therefore, it is fair to say that the best ventricular assist device design at present involves using a textured surface only at required sites within the blood-contacting surface of the ventricular assist device, with thrombus anchoring being carried out only at these sites, and/or with endothelial cells covering only these sites, while other sites have a minor-surface finish and/or are coated with an anti-thrombogenic coating. In light of the above, there is no doubt that, as well as being capable of manufacturing a ventricular assist device by appropriately selecting a smooth surface or a textures surface for each device, instrument, or component that makes up the ventricular assist device, it is also necessary to make it possible to manufacture a device, instrument, or component that comprises mixed textured surface portions and smooth surface portions.

CITATION LIST

Patent Literature

PTL 1: U.S. Pat. No. 6,050,975
PTL 2: US2007/0299297 A1

Non Patent Literature

NPL 1: H. Harasaki et al. Powdered Metal Surface for Blood pump. Trans Am Soc Artif Intern Organs, 1979; 25; 225-230

SUMMARY OF INVENTION

A first object of the present invention is to provide an inflow cannula for blood circulatory assist devices, having a robust structure and possessing a thrombus anchoring effect to allow thereby adhesion of endothelial cells to the inflow cannula, wherein the inflow cannula does not deform or exhibit loss of dimensional accuracy during the manufacture process.

A second object of the present invention is to provide the inflow cannula, comprising a textured surface formed by pores which have a uniform opening surface area and opening shape, whereby the thrombus anchoring effect is enhanced and the endothelial cells can be adhered to the inflow cannula even more stably as a result.

A third object of the present invention is to provide the inflow cannula having yet higher mechanical strength, and being yet easier to insert into the application site.

A fourth object of the present invention is to provide the inflow cannula for blood circulatory assist devices that, in addition, allows successfully inhibiting excessive proliferation of cells at the leading end of the inflow cannula.

A fifth object of the present invention is to provide a method for manufacturing an inflow cannula, wherein a structure is not deformed, and high dimensional accuracy is preserved, during the manufacturing process.

A sixth object of the present invention is to provide a connector for connecting a conduit and a blood pump in a blood circulatory assist device, wherein the connector has a robust structure and possesses a thrombus anchoring effect, and wherein the connector does not deform or exhibit loss of dimensional accuracy during the manufacturing process.

Further objects of the present invention are to provide a conduit assembly and a ventricular assist device having the inflow cannula, as well as a method of manufacturing the inflow cannula, and use thereof.

Other objects of the invention of the present application will become apparent from the disclosure below:

As a result of diligent research directed at achieving the above-described objects, the inventors found that the objects can be attained by forming a porous structure from one or more linear elements, or by using a porous shaped article.

To address the first object, therefore, the present invention relates to an inflow cannula for blood circulatory assist devices, comprising partly or wholly a porous structure, wherein the porous structure is formed of a linear element or a porous shaped article.

To address the second object, the present invention relates to the inflow cannula, wherein the porous structure is formed of one or more linear elements spirally wound to form a hollow tubular body.

To address the third object, the present invention relates also to the inflow cannula, further comprising a tubular non-porous support on its radially inward side.

To address the fourth object, the present invention relates also to the inflow cannula, further comprising a tubular non-porous support on its radially inward side, wherein the non-porous support has an abutment portion in the form of a rim at one end.

To address the fifth object, the present invention relates to a method for manufacturing an inflow cannula, the method comprising:
(a) a step of spirally winding a linear element around a tubular core from its one end toward the other end;
(b) a step of spirally winding the same or a different linear element on the spiral wound in step (a), so that the element intersects the linear element spirally wound in step (a), thereby forming a tubular structure;

(c) a step of sintering the tubular structure thus obtained from steps (a) and (b);

(d) a step of removing the core from the sintered tubular structure from step (c); and (e) optionally, a step of fitting a tubular non-porous support into the inside of the tubular structure from step (d), said tubular non-porous support having an outer diameter adapted in such a way that it enables the support to be fitted into the inside of the tubular structure and thereby to support the latter, and/or (f) optionally, a step of applying an antithrombogenic coating to the tubular structure from step (d) or to the entirety of the tubular structure fitted with the non-porous support from step (e).

To address the fifth object, the present invention relates also to a method for manufacturing an inflow cannula, comprising:

(a) a step of randomly charging one or more linear elements into a formwork comprised of a base, and inner and outer walls concentrically disposed on the base, and fixing the elements, thereby obtaining a tubular structure in the form of a nonwoven, and (b) optionally, a step of fitting a tubular non-porous support into the inside of the tubular structure from step (a), said tubular non-porous support having an outer diameter adapted in such a way that it enables the support to be fitted into the inside of the tubular structure and thereby to support the latter, and/or (c) optionally, a step of applying an antithrombogenic coating to the tubular structure from step (a) or to the entirety of the tubular structure fitted with the non-porous support form step (b).

To address the sixth object, the present invention relates also to a connector for connecting an inflow cannula or an artificial blood vessel and a blood pump in a blood circulatory assist device, wherein a porous structure is bonded on the inner surface of the connector, or closely fitted into the inside of the connector, and wherein the porous structure is formed of one or more linear elements or of a porous shaped article.

Furthermore, the present invention relates to a conduit assembly comprising an inflow cannula and/or the connector, and to a ventricular assist device comprising the conduit assembly.

Also, the present invention relates to use of the inflow cannula for blood circulatory assist devices, by connecting the inflow cannula directly or indirectly to a blood pump.

Further, the present invention relates to a method of treating or improving a symptom, disease, or disorder selected from the group consisting of congestive heart failure, dilated cardiomyopathy, ischemic heart disease, cardiac sarcoidosis, and cardiac amyloidosis, by using a ventricular assist device comprising the inflow cannula for blood circulatory assist devices.

Other aspects and preferred embodiments of the present invention for addressing the above-stated objects are set forth below and in dependent claims.

As used herein, the term "blood circulatory assist device" means a device for replacing or assisting the pump function of the heart in blood circulation, when the cardiac function of the patient is impaired owing to heart failure or the like.

As used herein, the term "ventricular assist device" means a device, among the above-defined "blood circulatory assist devices", for assisting circulation of patients still retaining their own heart. The ventricular assist device comprises mainly, for instance, a blood pump, a controller for regulating the function of the blood pump, a battery as a power supply source, and various conduits such as an inflow cannula, an outflow graft, an artificial blood vessel and so forth. The blood pump is connected to a portion of the heart either directly or indirectly via the inflow cannula and so forth, and pumps as a result blood into the body in a sufficient amount and with sufficient pressure.

As used herein, the term "inflow cannula" means a tubular-shaped instrument in the form of a conduit that is inserted into a ventricle or an atrium, preferably the left ventricle, of the heart, for blood draining, and which is connected to the blood pump directly or via an artificial blood vessel or the like. The inflow cannula has the role of supplying blood from a ventricle or an atrium (preferably, the left ventricle), into the blood pump. In particular, an inflow cannula used by being connected directly or indirectly to a blood pump of a ventricular assist device will be called herein "an inflow cannula for ventricular assist devices".

As used herein, the term "connector" means an instrument serving as a joint for connecting the blood pump and a conduit (inflow cannula, outflow graft, artificial blood vessel) in the ventricular assist device.

When the inflow cannula is directly connected to the blood pump, the connector joins the inflow cannula and the blood pump. When the inflow cannula is connected indirectly to the blood pump via an artificial blood vessel, the connector joins the artificial blood vessel and the blood pump. In addition to connecting the inflow cannula or artificial blood vessel to the blood pump, the connector may also be used as a joint for connecting the outflow graft and the blood pump.

As used herein, the term "conduit assembly" means an assembly comprising a conduit and/or a set of related parts, which are placed at a region between the heart and the blood pump in a ventricular assist device in order to feed the blood from a ventricle or an atrium of the heart to the blood pump. The essential constituent elements of the conduit assembly are the inflow cannula and the connector.

Therefore, when the inflow cannula is connected to the blood pump indirectly via the artificial blood vessel, the conduit assembly comprises the inflow cannula and the artificial blood vessel, as well as various parts for assembling and fixing, such as a connector for connecting the inflow cannula and the artificial blood vessel to the blood pump, a cuff, a sleeve, clamps, a holding ring and the like. When the inflow cannula is connected directly to the blood pump, the conduit assembly may comprise only the minimum constituent elements, namely, it may comprise only the inflow cannula and the connector for connecting the inflow cannula to the blood pump. In the case of such conduit assembly comprising only the inflow cannula and the connector, these may be directly connected one another, for example, by screwing one into the other. Alternatively, the conduit assembly may be manufactured integrally as a single instrument that comprises a portion functioning as the inflow cannula and a portion functioning as the connector.

In all cases, the conduit assembly has the function of draining blood from the heart and feeding the blood to the pump, and the function of connecting the conduit to the blood pump. These functions are ensured by arranging continuously (if necessary, via the artificial blood vessel) the inflow cannula and the connector within a same conduit assembly.

The inflow cannula of the present invention comprises a specific porous structure having open pores on part, most, or the entirety of the inflow cannula. The connector of the present invention has this specific porous structure in part of the connector, the porous structure being bonded on the inner surface of the connector, or closely fitted into the inside of the connector.

In one embodiment of the present invention, the above-described porous structure is formed by one or more linear elements.

When the above porous structure is formed by one or more linear elements, the porous structure comprises a porous texture having as constituent elements thereof one or more linear elements. The structure is formed herein through intersection and/or contact between one or more linear elements. Pores can be form at the regions surrounded by the lines that join mutually-adjacent intersection points and/or contact points of the one or more elements on the surface of the porous structure. Specifically, a porous texture is formed by, for instance, winding, weaving, or knitting one or more linear elements, or by arranging or entangling one or more linear elements irregularly so as to form a nonwoven. In this case, each linear element intersects and/or comes into contact with itself, or with a different linear element, countless times, on the surface of the structure, or both on the surface of the structure and the inward in the thickness direction of the structure. As a result, there form the regions surrounded by the lines that join mutually-adjacent intersection points and/or contact points among the resulting intersection points and/or contact points of the elements. Such regions, which are of various arbitrary shapes, for instance rectangular, triangular, rhomboidal, parallelogram-shaped, polygonal and the like, or exhibit an arbitrary combined shape of the foregoing, may constitute the pores of the above structure.

In another embodiment of the present invention, the porous structure is formed of a porous shaped article.

In the porous structure of the present invention, blood flows into the structure through pores in such a surface. The flow of blood slows down as it penetrates into the structure. The inflowing blood congeals inside the structure, giving rise to thrombi of moderate size. Thrombus anchoring is achieved thus in that the thrombi become held fast in the structure (In the specification of the present application, such thrombus holding within the structure is referred to as "thrombus anchoring".).

The "pores" have only to allow blood cells to pass through the pore, and the pores typically have an opening surface area no smaller than about $1.9 \times 10^{-5}$ mm$^2$ (about 5.0 micrometer in terms of circular diameter). The upper limit of opening surface area may be set ordinarily at about 20 mm$^2$ (about 5.0 mm in terms of circular diameter) in such a manner that the mechanical strength of the porous structure is maintained. Within the above-described range from about $1.9 \times 10^{-5}$ mm$^2$ to about 20 mm$^2$, the larger the opening surface area is, the more easily the blood flows into the structure. By contrast, a smaller opening surface area affords more stable thrombus anchoring, since in that case the thrombi are held more firmly inside the structure. A large opening surface area is advantageous in terms of easier processing during manufacture of the above-described porous structure. With all the above considerations in mind, therefore, the pores in one embodiment have preferably an opening surface area of about $0.22 \times 10^{-3}$ mm$^2$ to about 0.80 mm$^2$ (about 17 micrometer to about 1.0 mm in terms of circular diameter), for instance, an opening surface area of about $3.0 \times 10^{-2}$ mm$^2$ to about $15 \times 10^{-2}$ mm$^2$ (about 0.20 mm to about 0.44 mm in terms of circular diameter).

The opening surface area of the respective pores in the porous structure of the present invention can be determined mathematically on the basis of the geometrical shape and the dimensions of the respective pores, as measured on the basis of frontal close-up pictures of the structure, and after correction for magnification. Not all the pores formed in the structure need to have an opening surface area lying within the above-described range of about $1.9 \times 10^{-5}$ mm$^2$ to about 20 mm$^2$. So long as the desired purpose of the invention can be achieved, only a part of the formed pores need have a size lying within the above-described range. Preferably, however, the greater part of the pores, and preferably all or substantially all the pores have the above-described pore size.

Furthermore, "pores" can also be formed in the thickness direction of the porous structure of the present invention. That is, when the porous structure is formed of one or more linear elements, the elements can also form the above-described "pores" in the regions surrounded by the lines that join mutually-adjacent intersection points and/or contact points of the elements on a surface parallel to the thickness direction of the structure, depending on the number of linear element layers, the diameter of the linear elements and the manufacturing method. In addition, such "pores" can also be formed in the thickness direction depending on the thickness of the structure and the manufacturing method when the above porous structure is formed of a porous shaped article, An aspect in which such "pores" are formed in the thickness direction lies evidently also within the scope of the invention of the present application. Such pores in the thickness direction increase the space capable of holding thrombi in the structure, and hence, reinforce the anchoring effect.

As used herein, the term "porous structure" means a rod-like porous structure having a hollow interior. The cross-sectional shape of the porous structure is not particularly limited. For instance, the cross-sectional shape of the structure may be circular, oval, or polygonal (for instance, triangular or quadrangular), or may be roughly circular or roughly oval. The structure of the present invention, moreover, need not necessarily exhibit a constant diameter, thickness and cross-sectional shape throughout the entire structure. Therefore, the diameter, thickness and cross-sectional shape of the structure can be accommodated to the shape required of the structure when serving as a device or instrument, or to the shape of the device, instrument or the like in which the structure is disposed.

Whether the porous structure is used as an inflow cannula or as part of the connector, if the inner diameter of the structure is too large, the proportion of space occupied by the structure in the heart or the thoracic cavity becomes unnecessarily large. On the other hand, an excessively small inner diameter may preclude securing sufficient drainage. Therefore, the inner diameter of the porous structure ranges ordinarily from 6 to 30 mm, in particular from 10 to 20 mm.

The thickness of the porous structure depends, for instance, on the diameter of the linear element(s) and on the way the structure is made out of the one or more linear elements. However, in terms of securing sufficient space also in the thickness direction, for thrombus anchoring and for allowing endothelial cells to be adhered, the thickness of the porous structure may range ordinarily from 0.2 to 5 mm, in particular from 0.5 to 2 mm, whether the structure is used as an inflow cannula or as part of the connector.

When the porous structure is used as an inflow cannula, the length of the structure can be appropriately set in accordance with the length of the portion of the structure, which runs through the ventricle wall or atrium wall and is exposed into the heart (for instance, into the left ventricle), and/or taking into account the need for securing sufficient drainage. If the exposed portion is too short, however, the opening at the leading end of the structure may become blocked by surrounding tissue and muscular tissue growth. Such being the case, the length of the structure ranges ordinarily from 10 mm to 50 mm, in particular from 15 mm to 35 mm.

When the structure is used as part of the connector, the length of the structure is appropriately set so as to match the form of the connector.

As used herein, the term "linear element" means a metallic linear material and a non-metallic linear material.

A linear element that can be used in the porous structure of the present invention may be, for instance, metallic linear elements, polymeric linear elements, or carbon fibers.

Although not particularly limited thereto, examples of materials for the metallic linear element include, for instance, stainless steel, pure titanium, or titanium alloy. Examples of materials for the polymeric linear element include, for instance, polyesters, polyamides, polypropylene, fluororesins and the like.

Considering all factors such as the strength of the material itself, biocompatibility, ease of workability and so forth, it is preferable to use pure titanium or titanium alloy as the material of the linear element. In the porous structure of the present invention, the cross-sectional shape that is obtained when cutting the linear element in a plane perpendicular to the longitudinal direction of the element may be in principle any cross-sectional shape. In terms of achieving a smooth flow of blood into the structure via the pores, there are preferably used one or more linear elements having a smooth surface, with no angles.

When the porous structure made of one or more linear elements is fixed by way of, for instance, sintering or the like during the manufacturing process of the structure, it is preferable to use linear elements that yield a large contact surface area at the intersection points and/or contact points of the elements, with a view to increasing the mechanical strength of the structure obtained after sintering.

In light of the above, the porous structure of the present invention uses preferably one or more linear elements having a flattened oval cross section (hereinafter, "flattened linear element" for short). Such flattened linear element can be manufactured, for instance, through rolling of a linear element having a circular cross-sectional shape. In the present invention, there are ordinarily used one or more flattened linear elements each having a flattening of 1.1 to 10, the flattened linear elements being obtained by rolling respective linear elements of circular cross-sectional shape.

As used herein, the term "flattening" means the ratio between the short diameter and the long diameter in the cross-sectional shape of the flattened linear element, i.e., the value obtained by dividing the long diameter by the short diameter of the cross-sectional shape (the long diameter/the short diameter ratio). In the present invention, there are preferably used one or more flattened linear elements each having a flattening ranging from 1.1 to 5, and more preferably, in particular, flattened linear elements each having a flattening ranging from 1.5 to 2.5, with a view to increasing the contact surface area between linear elements.

If the diameter of the linear element used in the porous structure of the present invention is too small, mechanical strength is impaired, while too large a linear element diameter detracts from workability. Hence, preferably, the linear element used has a diameter ranging from 20 micrometer to 500 micrometer. In particular, the used linear element has a diameter ranging from 30 micrometer to 200 micrometer from the viewpoint of the handleability of the porous structure (for instance, taking into account occurrences such as tearing of surgical gloves during surgery for placing the device in the patient, if the unevenness of the structure surface is excessive). This diameter is a value corresponding to a circle diameter, when the cross-sectional shape of the linear element is circular, a short diameter when the cross-sectional shape is an oval or flattened oval shape, and a short side, when the cross-sectional shape is rectangular.

Examples of linear elements that are used in the porous structure of the present invention include, for instance, a pure titanium wire complying with ASTM F67-95-Gr.2 (obtained by rolling a wire having a diameter of 85 plus/minus 20 micrometer to a thickness of 50 plus/minus 20 micrometer), or titanium alloys wires complying with the specifications Ti-6Al-4V alloy ELI, Ti-6Al-7Nb, Ti-13Zr-13Nb, Ti-15Mo-5Zr-3Al or Ti-6Al-2Nb-1Ta (obtained by rolling a wire having a diameter of 85 plus/minus 20 micrometer to a thickness of 50 plus/minus 20 micrometer), as well as polyester fibers.

When the porous structure of the present invention is formed of linear elements, the structure may be manufactured using one or more such linear elements. When using two or more linear elements, all the linear elements may be of identical material, or there may be used a combination of linear elements of dissimilar materials. Whether in the case of using one linear element or using two or more linear elements for manufacturing one porous structure, there is(are) preferably used seamless linear element(s) having a smooth surface, with a view to reducing biased blood flow on the structure surface and to smoothen the inflow of blood into the structure via the pores.

In an embodiment, the porous structure of the present invention can be formed by winding one or more linear elements into a hollow tubular body.

In this case, the porous structure can be manufactured, for instance, by randomly or spirally winding numerous times one or more linear elements around a tubular core made of ceramics, so that the above-described pores are formed, and so that numerous layers of the linear elements are formed, followed by sintering, after which the core is removed.

To manufacture the porous structure by winding the one or more linear elements into a spiral shape, the linear elements can be wound with S winding and/or Z winding, for instance, and can be wound with alternating S and Z winding.

Specifically, for instance, one linear element is wound (winding direction: S winding) into a spiral shape around a tubular core, from its one end toward the other end, at an appropriate pitch, such that upon reaching the other end, the winding reverses and the linear element is spirally wound (winding direction: Z winding) in such a manner so as to intersect the above spiral that had been wound theretofore. Such linear element winding is repeated until obtaining a desired number of layers (thickness of the structure). As a result, there can be obtained a structure in which the above-described linear element is spirally wound numerous times in a manner that numerous layers of the linear element are formed.

If using a plurality of linear elements, for instance, one linear element is wound into a spiral shape around a tubular core, from its one end toward the other end, at an appropriate pitch. Over that linear element, another separate linear element is spirally wound at an appropriate pitch in a reverse winding direction. Thereby there can be manufactured a tubular structure in which the linear elements are wound spirally numerous times in a manner that numerous layers of the linear elements are formed. In other words, such a tubular structure can be also manufactured by using different linear elements at each layer.

In a porous structure thus obtained, as illustrated in FIG. 1A, pores are formed by the intersections of one or more linear elements. The pores of the structure are formed by the regions surrounded by mutually-adjacent intersection points on a plane, among the intersection points of the one or more linear elements (see the shaded area in FIG. 1A).

The terms "S winding" and "Z winding" mean concepts pursuant to "S lay" and "Z lay" defined in JIS G 3525 "Wire Ropes". That is, "S winding" means linear element winding in the same direction as that of the "S lay", while "Z winding" means linear element winding in the same direction as that of the "Z lay". Also, the term "pitch" means the distance traveled in the axial direction in one turn of the spiral, when the one or more linear elements are wound into a spiral shape. For instance, the pitch may range from 10 to 20000 micrometer.

Sintering is carried out at a temperature under the melting point of the material of the used linear element(s), but at such a temperature and for over such a sintering time as to allow ensuring strong enough bonding at the intersection and/or contact points of the linear element(s). For instance, when using pure titanium linear element, sintering can be carried out ordinarily at 1200 to 1300 degrees Celsius for about 0.5 to 5 hours. The sintering oven is not particularly limited, but there may be used an infrared radiation-type or induction heating-type vacuum furnace. In the sintering step, the intersections and/or contact portions in the respective linear elements become completely bonded. As a result, the linear elements do not come apart, and there can be obtained a structure having high mechanical strength.

The porous structure of the present invention can be manufactured by randomly charging the one or more linear elements into a formwork (for instance, a ceramic formwork) comprised of a base, and inner and outer walls concentrically disposed on the base, and fixing the elements, to obtain thereby a sheet-like nonwoven of tubular shape having the above-described pores. In another embodiment, one or more linear elements are woven or knitted, followed by sintering for the bonding between respective linear elements, to manufacture a sheet-like knitted or woven having the pores, out of the linear elements. In order to manufacture the porous structure, the sheet-like knitted or woven is rolled up into a tubular shape or is rolled around a tubular core, and thereafter, the two end sides are welded together, and then the core is pulled out, in case of using such a core. The porous structure can also be formed by stacking two or more plies of these sheet-like knitted, woven, or nonwoven.

Herein, the term "fixing" refers to processing the one or more linear elements charged randomly into the above-described formwork, in such a manner that the fabric of the nonwoven becomes fixed. This fixing process can be carried out by, for instance, pressing, sintering, welding, pressure-bonding, or adhesive bonding. The fixing process is not particularly limited provided that the elements can be fixed.

The term "knitted" means a fabric-like body that becomes knitted while knitting stitches are made using the above-defined linear element(s). The term "woven" means a body, finished to a sheet shape, resulting from combining one or more linear elements as defined above longitudinally and transversally, and mixing the elements according to a given rule. The term "nonwoven" means a body formed using as a base material one or more linear elements as defined above, arraying or entangling the elements irregularly such that the elements are oriented unidirectionally or randomly. The linear element(s) in the knitted, woven, and nonwoven is(are) bonded to itself or bonded to one another by sintering or the like.

In a porous structure manufactured from a sheet-like nonwoven, the one or more linear elements intersect and/or come into contact with each other as illustrated in FIG. 1B, so that the above-described pores of the structure are formed by the regions (shaded area in FIG. 1B) surrounded by the lines that join mutually-adjacent intersection points and/or contact points on a plane, among the resulting intersection points and/or contact points of the elements.

With a view to enhancing mechanical strength and increasing the surface area per unit volume, the structure thus manufactured may be used after being dipped in an alkaline aqueous solution of concentration no higher than 7N, preferably no higher than 5N, preferably a sodium hydroxide solution, at a temperature of 25 to 100 degrees Celsius, preferably at 60 degrees Celsius, for 1 to 8 hours, followed by washing for 0.5 to 5 minutes with distilled water at room temperature.

This fixing process can be carried out by any conventionally known method, for instance, pressing, sintering, welding, pressure-bonding, or adhesive bonding. Specifically, if sintering is performed as the fixing treatment, sintering may be carried out under conditions as described above.

As used herein, the term "porous shaped article" means a shaped article obtained by shaping a metallic material, a resin material or the like into a hollow tubular body, in such a way that the surface of the shaped article, or both the surface and the interior of the shaped article, has a plurality of pores.

As the metallic material or resin material, there can be used, although not limited thereto, for instance, stainless steel, pure titanium or titanium alloys, fluororesins or the like.

Considering all factors such as the strength of the material itself, biocompatibility, ease of workability and so forth, it is preferable to use pure titanium or titanium alloy as the material of the porous shaped article. Examples of the materials include, for instance, pure titanium complying with ASTM F67-95-Gr.2, or a titanium alloy complying with specifications Ti-6Al-4V alloy ELI, Ti-6Al-7Nb, Ti-13Zr-13Nb, Ti-15Mo-5Zr-3Al, or Ti-6Al-2Nb-1Ta.

For instance, if using a metallic material, the above-stated porous shaped article can be manufactured as follows: A metal powder and a spacer material powder that evaporates at low temperature are mixed, and the mixture is molded into a hollow tubular body. Next, the spacer material is vaporized through heating to the evaporation temperature of the spacer material powder, followed by sintering at a sintering temperature higher than the evaporation temperature, to sinter the metal powder. Metallic materials having pores formed therein through active introduction of voids on the surface and the interior by, for instance, using such a spacer material, are also called "porous metals".

As the spacer material, there can be used, for instance, ammonium hydrogen carbonate, urea, a polyoxymethylene resin, a urea resin, a foamed polystyrene resin, or a foamed polyurethane resin. These materials can be used, for instance, in the form of spherical, columnar, or fibrous powders.

Sintering can be carried out under the same conditions as in the case where one or more linear elements are used. For instance, if using pure titanium as the metal powder and a polyoxymethylene resin as the spacer material, heating is ordinarily carried out, in order to evaporate the spacer material, at from 300 to 500 degrees Celsius, for 0.5 to 5 hours, after which sintering is carried out ordinarily at from 1200 to 1300 degrees Celsius for about 0.5 to 5 hours.

An antithrombogenic coating can also be applied to the surface of the one or more linear elements or of the porous shaped article in the porous structure manufactured as described above. Applying an antithrombogenic coating allows preventing thrombi anchored in the structure from becoming excessively large, and allows preventing, as a result, thrombus anchoring from becoming unstable. In this regard, for instance, an MPC polymer coating can be used as the antithrombogenic coating. The structural unit of the MPC polymer is MPC (2-methacryloyloxyethyl phosphorylcholine), which has a polar group structure identical to that of phosphatidylcholine comprised in the cell membrane. As a result, when the MPC polymer is coated on the porous structure, a structure similar to a cell membrane forms on the surface of the porous structure. This cell membrane-like structure affords thus antithrombogenicity by inhibiting the adhesion of platelets and the like. MPC is commercially available.

The antithrombogenic coating can be applied in accordance with any known method regarding coating for imparting antithrombogenicity to the surface of a material. For instance, the procedure below can be carried out if the antithrombogenic coating is an MPC coating:

MPC is diluted in ethanol to prepare a 0.1 to 10 wt %, preferably 0.5 wt % MPC ethanol solution.

The manufactured porous structure is soaked in this solution, at room temperature, for 1 to 60 minutes, preferably 5 to 10 minutes.

The structure is taken out of the solution and is dried at room temperature.

The porous structure of the present invention ordinarily has a porosity of 5 to 90 vol %, preferably of 30 to 80 vol % in terms of striking a balance between the mechanical strength of the entire structure on one hand, and securing space for holding thrombi and/or for allowing endothelial cells to be adhered on the other hand. Herein, "porosity" means the proportion (vol %) of the volume of empty space relative to the entire volume of the above-described structure. This porosity can be determined approximately as follows:

An average geometrical shape for the porous structure is assumed (for instance, a hollow cylinder having a uniform thickness in the radial direction), and the volume ($V_1$) of the geometrical shape is calculated mathematically.

The weight of an actual structure manufactured using one or more linear elements, or of an actual porous shaped article, is measured.

The volume ($V_2$) of the linear elements portion or of the porous shaped article portion in the structure is determined from the above weight and the specific gravity of the linear elements or of the shaped article.

The total void volume ($V_3$) of the structure is determined by subtracting the volume ($V_2$) of the linear elements portion or of the shaped article portion from the volume ($V_1$) of the assumed geometrical shape.

The total void volume ($V_3$) of the structure is divided by the volume ($V_1$) of the assumed geometrical shape, and the resulting value is multiplied by 100 to yield the porosity (vol %).

The porosity can be controlled. For instance, when the structure is manufactured by winding one or more linear elements into a hollow tubular shape, the porosity can be controlled by adjusting, for instance, the diameter of the used linear elements, the pitch at which the linear elements are wound, and the number of layers of wound linear elements. When manufacturing the porous structure using a sheet-like nonwoven in the form of a hollow tubular body, comprising one or more linear elements, the porosity can be controlled mainly by adjusting the packing density of the linear elements.

In addition, when the porous structure is formed of a porous shaped article, porosity can be controlled by adjusting the mixing ratio of the metal powder and the spacer material powder, or by adjusting the average particle size of the spacer material powder.

The porous structure of the present invention thus manufactured from one or more linear elements or being formed of a porous shaped article is robust, and hence, there is very little risk that, during use in vivo, part of the structure material will come off and get into the bloodstream. Therefore, the porous structure of the present invention has extremely high mechanical strength and can dwell safely in vivo for long periods of time, for instance, from several months to several years.

In the porous structure of the present invention, moreover, the layer structure of the structure can be easily controlled by appropriately selecting, for instance, the form (in particular the diameter) of the linear element(s), and/or the number of layers formed by wound linear element(s) during the manufacturing process of the structure, in the case of the structure manufactured through linear element winding. In the case, for instance, of a tubular structure comprising a sheet-like nonwoven manufactured using linear element(s), the layer structure can be easily controlled by appropriately selecting, for instance, the form (in particular the diameter) of the linear element(s) and the layering thickness of the wound linear element(s) during the manufacturing process of the structure. Furthermore, if the porous structure comprises a porous shaped article, the thickness of the structure can be easily controlled by appropriately selecting, for instance, the formwork that is used during the shaping process. Through adjustment of the porosity by forming multiple pores not only in the planar direction but also in the thickness direction, the above-described porous structure easily affords thus a three-dimensional structure having voids of a moderate size also in the thickness direction, i.e., allows easily obtaining a three-dimensional structure where sufficient space can be secured for holding thrombi and/or for allowing endothelial cells to be adhered. As a result, a high anchoring effect is achieved, and furthermore, if the porous structure is placed at sites neighboring living tissue, stable adhesion of endothelial cells to the structure is achieved.

In particular, in the case of a porous structure manufactured through spiral winding of one or more linear elements at a constant pitch, the opening shape and the opening surface area of the pores in the structure is uniform, and furthermore, the three-dimensional structure of the structure as a whole is also homogeneous, with voids of moderate size. Also, the ultimately manufactured structures exhibit very little variation among individual structures.

It has been found that extremely stable thrombus anchoring can be achieved by way of a porous structure that is manufactured thus in such a way so as to have a uniform opening shape and opening surface area, and so that the three-dimensional structure of the structure as a whole is homogeneous and has voids of moderate size. In addition, it has been also found that, if the structure is used at sites neighboring living tissue, for instance, in the heart, fibroblasts which enter via the pores of the structure are adhered in the voids of the structure, and endothelial cells growing from heart muscle very homogeneously cover the entire surface of the structure, just as they do in a living body, as a result of getting onto the fibroblasts.

This is believed to be the result of early stabilizing of thrombus adhesion at the voids in the porous structure, prior to extension of the endothelial cells. Upon adhering to the structure, the thrombi are shrunk by the fibrinolytic system. This early-stage thrombus adhesion/shrinkage process progresses uniformly throughout the entire structure. It would appear that, when early thrombi are thus adhered, endothelial cells enter and become further adhered to the adhesion sites of the early thrombi, and therefore extension of the endothelial cells also progress uniformly across the entire structure, as a result of which there forms an extremely uniform and stable endothelial cell tissue.

Specifically, if the porous structure is used as an inflow cannula (or part thereof) in, for instance, the left ventricle, endothelial cells extend from the inner face of the left ventricle towards the outer peripheral face of the inflow cannula. Ordinarily, each endothelial cell undergoes about 50 to 100 cell divisions. This number of cell divisions is sufficient to cover with cells the entire outer peripheral face of an inflow cannula having an ordinary size.

As for the porous structure covered with endothelial cells, the possibility of blood coagulation is exhausted, and extremely high antithrombogenicity is elicited. This is believed to arise from the control carried out by the endothelial cells themselves in such a manner that no thrombi at all form on vascular endothelial cells or around vascular endothelial cells, or in such a manner that any thrombi that for some reason do form are quickly dissolved. This control is a capability of vascular endothelial cells, that is elicited mainly through regulation of the expression level of t-PA (tissue plasminogen activator) and/or PAI-1 (plasminogen activator inhibitor-1). Normally, this capability is referred to as vascular endothelial cell antithrombogenicity, and constitutes a very important function among the many functions of vascular endothelial cells.

If the porous structure is covered with such endothelial cells, moreover, foreign bodies such as germs are prevented from intruding into the porous structure. This reduces the risk of infection, which is a frequent problem when using indwelling medical devices such as artificial hearts or ventricular assist devices, and which can be a life-threatening problem for the patient.

Benign granulation tissue covers the structure, thereby inhibiting the growth of thrombi, and the structure can elicit thus high antithrombogenicity, even in cases where endothelial cells do not grow over the entire surface of the structure, for instance, when the placement site of the porous structure is a site distant from the heart muscle or when the patient in whom the structure is placed is an elderly patient.

The porous structure of the present invention is made of one or more linear elements or is formed of a porous shaped article. Therefore, the porous structure of the invention is advantageous in that the structure can be manufactured independently even without using a member such as the above-described wall shell, unlike the case when using the sintered titanium spheres disclosed by, for instance, H. Harasaki et al.

Therefore, the porous structure can be manufactured independently, for instance, as a device or instrument having a textured surface. Furthermore, the porous structure may be manufactured separately, and be then disposed/fixed to a desired site of a blood-contacting surface of a ventricular assist device. In this case, the device, instrument or the like in which the porous structure is placed needs not be treated in a sintering furnace, and it is enough to dispose the structure, manufactured separately, on the site that is to be imparted a textured surface. Hence, the device, instrument or the like does not suffer deformation, chapping, loss of dimensional accuracy or the like, and thus does not require additional processing using, for instance, an abrasive powder, a cutting powder or the like. It becomes thus possible to manufacture easily a device, instrument or the like having mixed smooth surface portions and textured surface portions.

As described above, the porous structure of the present invention can be manufactured on its own. Therefore, there is no fear of loss of dimensional accuracy of the porous structure itself on account of deformation and/or buckle in other members during sintering. Furthermore, the porous structure is free of design constraints due to other members such as the above-described wall shell, and hence the porous structure can be assembled with good accuracy into the device, instrument, or component.

In one embodiment of the present invention, the inflow cannula of the present invention further comprises a tubular non-porous support that is fitted into the inside of the porous structure, said tubular non-porous support having an outer diameter adapted in such a way that it enables the support to be fitted into the inside of the tubular structure and thereby to support the latter.

In one embodiment, the support may comprise a support trunk portion which is centrally located, an abutment portion at one end, and a screw portion at the other end. The trunk portion is a portion that supports the porous structure. The length of the trunk portion corresponds to the length of the structure. The abutment portion is a rim portion provided in one end of the support. The abutment portion functions as a stopper when the support is fitted into the structure. The screw portion, which is provided at the other end of the support, is used for mounting other inflow cannula members and for mounting to an artificial blood vessel or a blood pump.

In addition to playing the role of stopper, the support abutment portion in the form of a rim has also the function of inhibiting excessive growth of tissue/cells. Although one effect of the structure is to cause endothelial cells and the like to get into the structure and become adhered therein, excessive growth of such endothelial cells can give rise to blood pooling regions, which may increase the risk of infarction. Therefore, excessive growth of endothelial cells or the like is inhibited by disposing the non-porous support abutment portion at the leading end side of the structure, which prevents as a result the inflow cannula from becoming occluded. In turn, this allows ensuring sufficient blood drainage.

In order to maximize the inhibitory effect on such excessive tissue/cell growth, the support abutment portion, in particular, the outer peripheral face of the support abutment portion, is preferably smoothed through polishing.

It is believed that excessive growth of tissue/cells on the outer peripheral face of the support abutment portion is inhibited when the Ra of the outer peripheral face is no greater than 1 micrometer. The Ra of the outer peripheral face is preferably no greater than 0.1 micrometer.

Herein, "Ra" means an arithmetic average roughness Ra as defined in JIS B 0601. The value of Ra can be measured using various commercially available contact- or non-contact-type measuring instruments. Specifically, for instance, the Ra value can be measured using a contact needle-type surface roughness tester, and setting a cutoff value of 0.25 mm, a measurement length of 1.25 mm, a measurement speed of 0.5 mm/s.

The overall length of the support, the width of the support trunk portion, the support abutment portion and the support screw portion, as well as the outer diameter, inner diameter, thickness and so forth of the foregoing are suitably set from the viewpoint of, for instance, matching with the shape of the porous structure, and in accordance with the inner diameter of the inflow cannula.

As described above, one purpose of the support abutment portion is to inhibit excessive growth of tissue/cells. Accordingly, the support abutment portion fails to elicit this inhibitory effect if its width is too short, while if its width is excessive, there increase the portions not covered by endothelial cells, which weakens the effect afforded by the structure. With the above in mind, the width of the support abutment portion ranges preferably from 0.5 mm to 15 mm, in particular from 1 mm to 5 mm.

The height of step between the outer peripheral face of the porous structure and the outer peripheral face of the support abutment portion should be as small as possible in order to reduce the force necessary for inserting the inflow cannula into the heart (ventricle or atrium) or for removing the inflow cannula therefrom, and in order to reduce damage to living tissues. Specifically, the outer diameter difference between the porous structure and the support abutment portion, preferably, ranges from 0 to 1 mm and is more preferably kept between 0 and 0.5 mm.

In an inflow cannula having such a support, the inner diameter of the support corresponds to the inner diameter of the inflow cannula. Therefore, a preferred inner diameter of the support may be identical to the values described above regarding the porous structure.

In this case, the outer diameter of the entire inflow cannula (diameter resulting from adding the thickness of the porous structure to the outer diameter of the support trunk portion) may range typically from 6 mm to 30 mm. Within this outer diameter range, the inflow cannula can be used in vivo without any problems.

In terms of mechanical strength, biocompatibility, ease of workability and so forth, pure titanium, stainless steel, a titanium alloy and the like can be used as the material of the support.

The inflow cannula comprising the support can be assembled, for instance, as follows.

The support is fitted into the radially inward side of the porous structure, until the support abutment portion butts the porous structure.

A sleeve and a cuff are strung in this order on the support, and lastly a cuff locking nut is screwed onto the support screw portion, to fix thereby the porous structure onto the support.

The antithrombogenic coating may also be applied onto the non-porous support. The antithrombogenic coating may be applied beforehand to the non-porous support. Alternatively, the antithrombogenic coating may be applied collectively on both the non-porous support and the porous structure after the non-porous support is fitted into the porous structure.

In an inflow cannula provided with the above-described non-porous support on the radially inward side of the cannula, one further porous structure according to the present invention may be disposed additionally on the radially inward side of the support.

The porous structure of the present invention can be used, for instance, as a device, an instrument or a component, or as a part of a device, an instrument or a component that makes up a ventricular assist device. In addition, the porous structure of the present invention can be used by being disposed on a device, an instrument or a component that makes up a ventricular assist device. In particular, the effect of the porous structure of the present invention can be brought out to the full when used at a site in the ventricular assist device, which comes into contact with blood.

Specifically, the porous structure of the present invention can be used, for instance, on the inner surface of a connector that connects the blood pump with an inflow cannula or an artificial blood vessel in a ventricular assist device, or can be used as an inflow cannula (or as part of an inflow cannula). Also, the porous structure of the present invention can be used in the inner wall and/or an impeller of the blood pump of a ventricular assist device.

BRIEF DESCRIPTION OF DRAWINGS

FIG. 1A shows pores in a porous structure manufactured by winding a linear element into a spiral shape (One pore in the porous structure is shown as the shaded portion). FIG. 1B shows pores in a porous structure manufactured using a sheet-like nonwoven (One pore in the porous structure is shown as the shaded portion).

DESCRIPTION OF EMBODIMENTS

Figure 1:
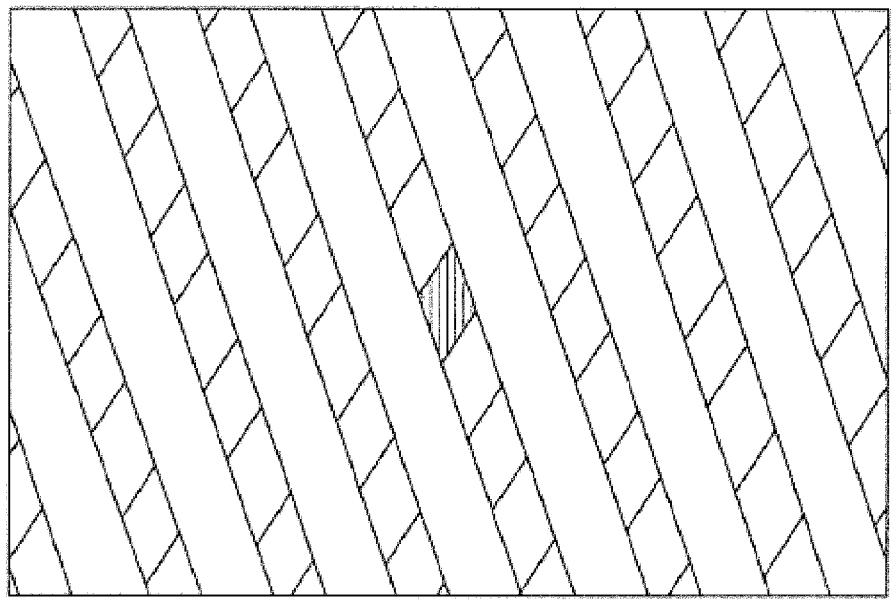
FIG. 1 is a set of diagrams illustrating pores in the porous structure of the present invention.
Figure 1:
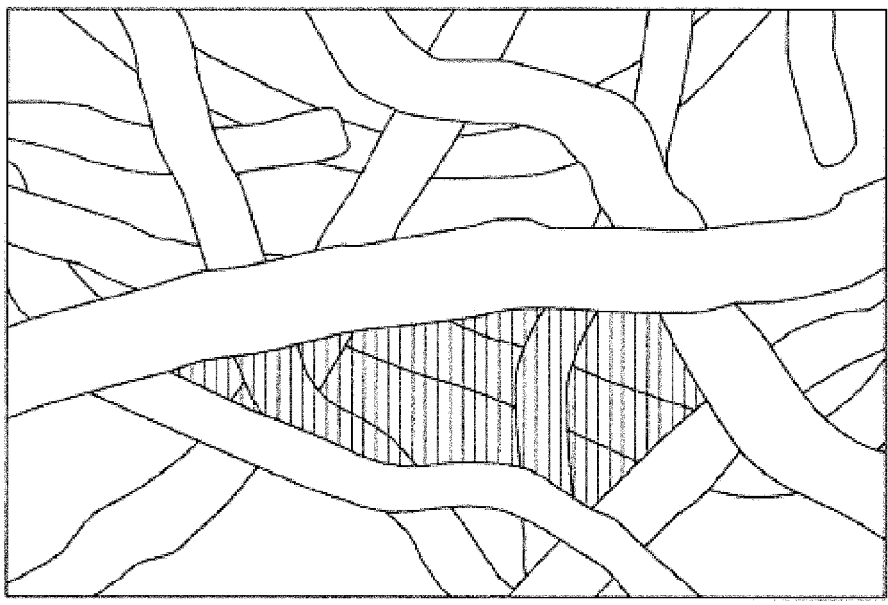
Figure 2:
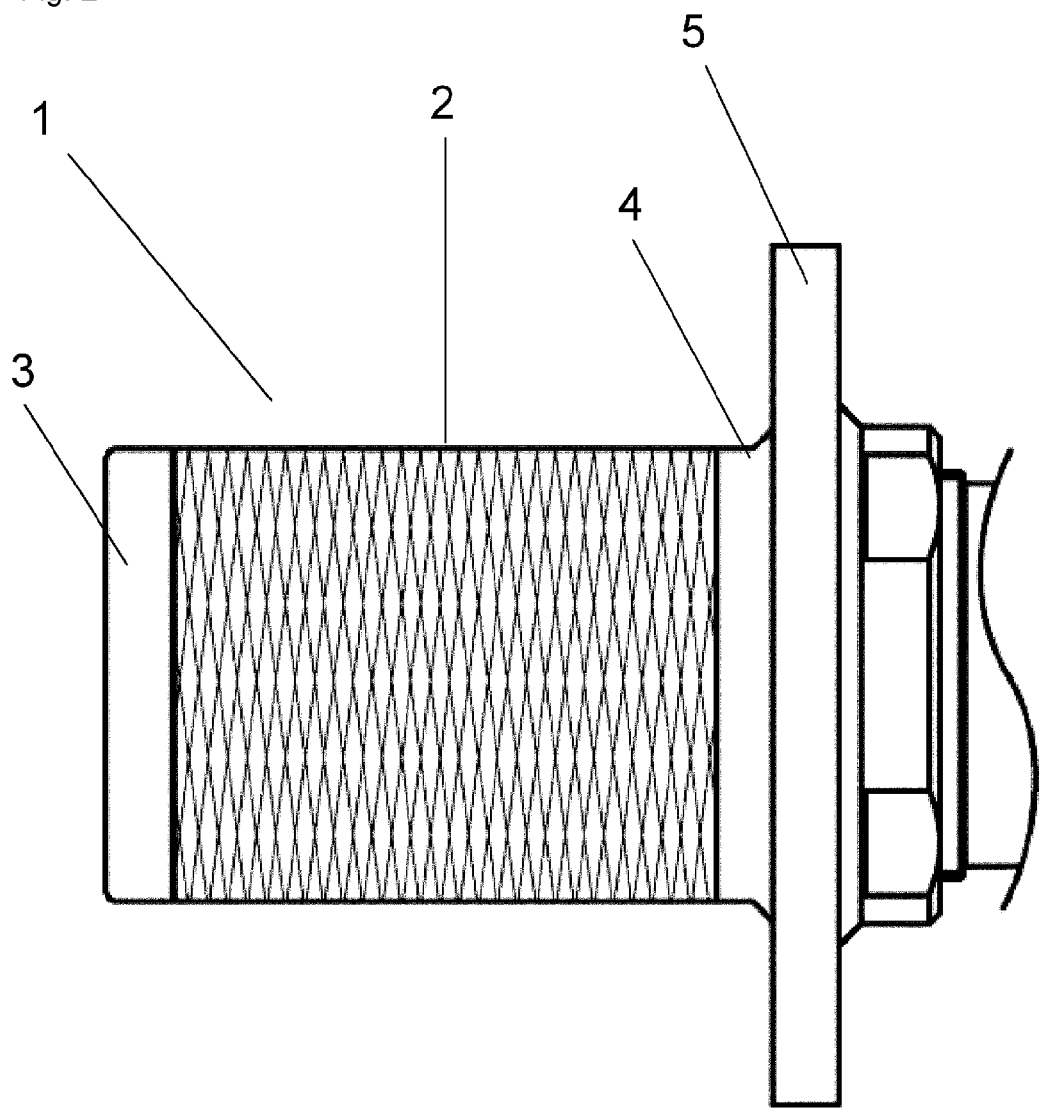
FIG. 2 is a diagram illustrating the inflow cannula of the present invention.

FIG. 2 is a diagram illustrating the inflow cannula of the present invention having a non-porous support, as an example of the present invention.

In FIG. 2, the reference numeral 1 denotes an inflow cannula for ventricular assist devices, provided with a support, that is inserted into a ventricle of the patient, most preferably into the left ventricle. The inflow cannula 1 comprises an inflow cannula main body 2 in the shape of a tubular porous structure, and a support 3 (non-porous tubular body made of pure titanium and having a smooth surface). In FIG. 2, the reference numeral 4 denotes a sleeve made of pure titanium, and 5 a cuff comprising PTFE fibers.

The outer peripheral face of the support abutment portion 3 has a Ra no greater than 0.1.

The main body 2 is obtained by winding one pure titanium wire into a spiral shape on a (ceramic-made) tubular core, with repeated S winding and Z winding, followed by sintering and removal of the core after sintering.

As illustrated in FIG. 2, the main body 2 comprises wire intersections, formed of pure titanium wire, and, in the main body 2, where pores are formed. In the main body 2 (length: 24 mm, outer diameter: 20 mm, inner diameter: 18.6 mm, thickness: 0.7 mm), the opening surface area of the pores ranges from about $3.9 \times 10^{-2}$ mm$^2$ to about $13.4 \times 10^{-2}$ mm$^2$. The main body 2 has an overall porosity of about 40 to about 70 vol %.

Figure 3:
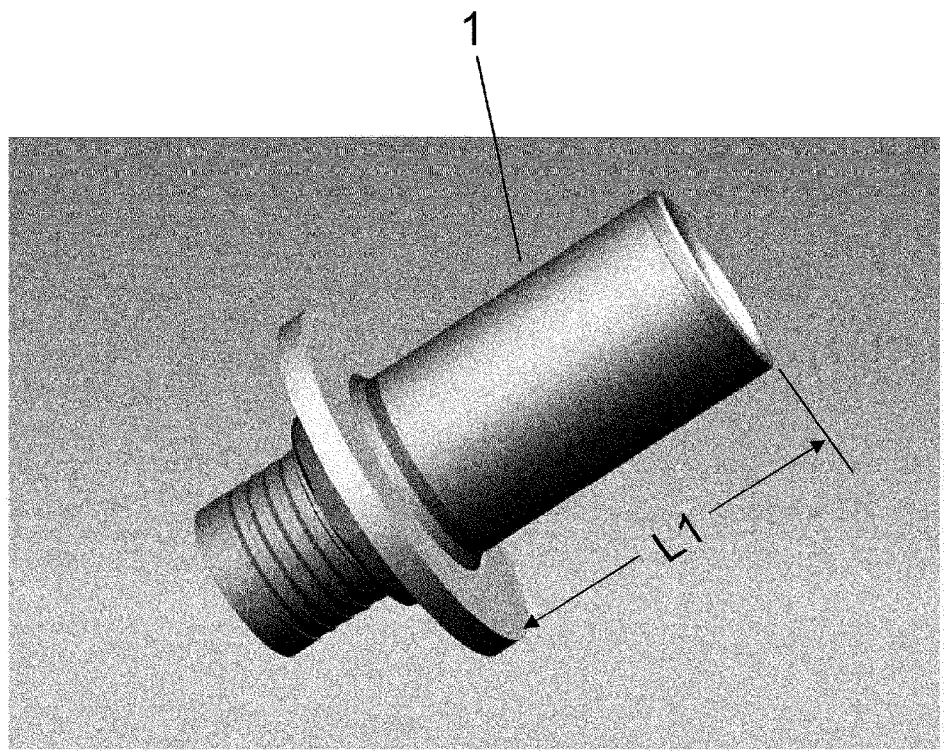
FIG. 3A is a perspective-view diagram of the inflow cannula illustrated in FIG. 2.
FIG. 3B is an exploded-view diagram of the inflow cannula illustrated in FIG. 2.
Figure 3:
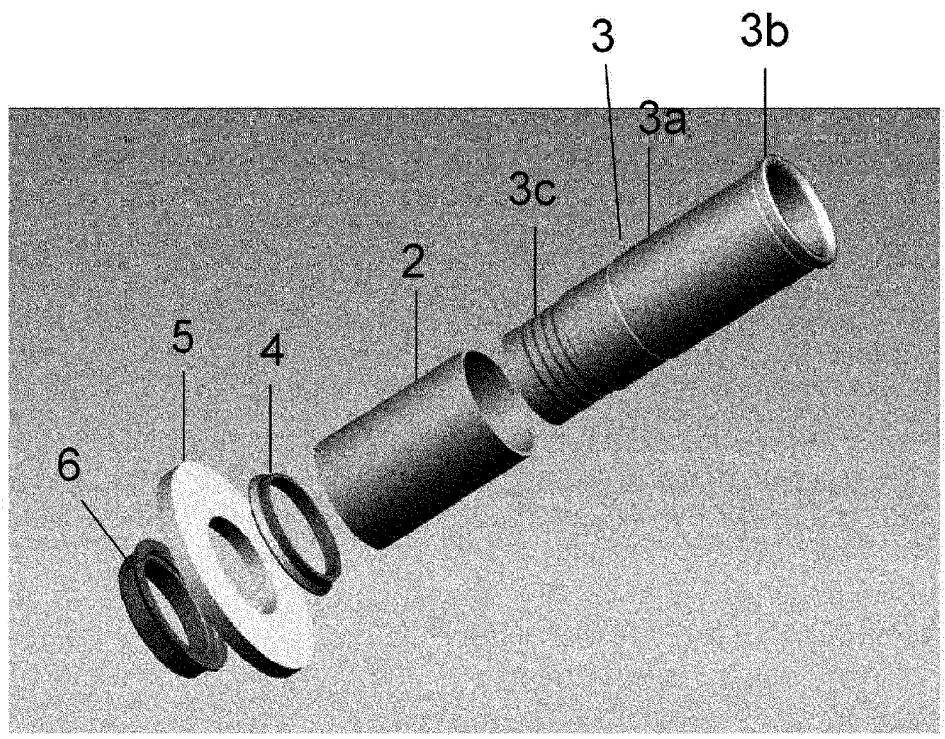

FIG. 3 includes a schematic diagram (FIG. 3A) and an exploded diagram (FIG. 3B) of the inflow cannula 1 illustrated in FIG. 2.

As illustrated in FIGS. 3A and 3B, in the inflow cannula 1, the support 3 is fitted into the inside of the main body 2. The entire length L1 (FIG. 3A) of the inflow cannula 1 is 30 mm.

The support 3 (total length: about 50 mm) comprises a support trunk portion 3a (outer diameter: 18.6 mm, inner diameter: 16 mm), an abutment portion 3b (outer diameter: 20 mm, inner diameter: 16 mm) and a screw portion 3c (outer diameter: 18 mm, inner diameter: 16 mm). The support trunk portion 3a has a slightly smaller outer diameter than the inner diameter of the main body 2, and therefore can be fitted into the main body 2, appropriately matched to the body 2. In addition, the support 3 comprises the abutment portion 3b having an outer diameter slightly greater than the outer diameter of the support trunk portion 3a. This abutment portion 3b plays the role of a stopper during fitting into the main body 2, so that the main body 2 can be fixed firmly on the support by clamping the main body 2 between the abutment portion 3b and a sleeve 4 (and/or a cuff 5, a cuff locking nut 6). The inflow cannula 1 is connected to an artificial blood vessel or a blood pump via the screw portion 3c.

An MPC polymer coating is applied over the entire main body 2 and the support 3.

Figure 4:
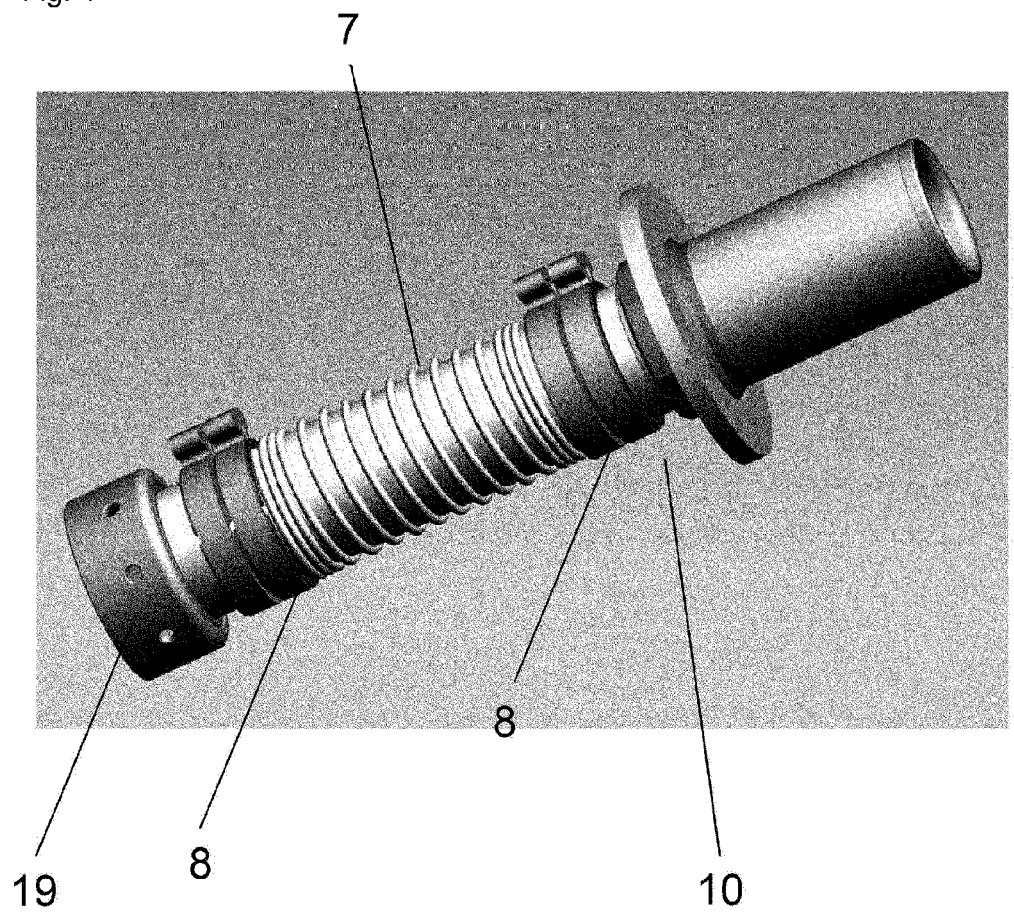
FIG. 4 is a perspective-view diagram of a conduit assembly comprising the inflow cannula illustrated in FIG. 2.

As illustrated in FIG. 4, the inflow cannula 1 is connected to an artificial blood vessel 7 via the support screw portion 3c. The inflow cannula 1 constitutes a conduit assembly 10, together with the artificial blood vessel 7, an outer clamp 8, an inner clamp 9, a connector 18, and a holding ring 19 (see also FIGS. 5, 11, and 12), and is ultimately connected to the blood pump.

Figure 5:
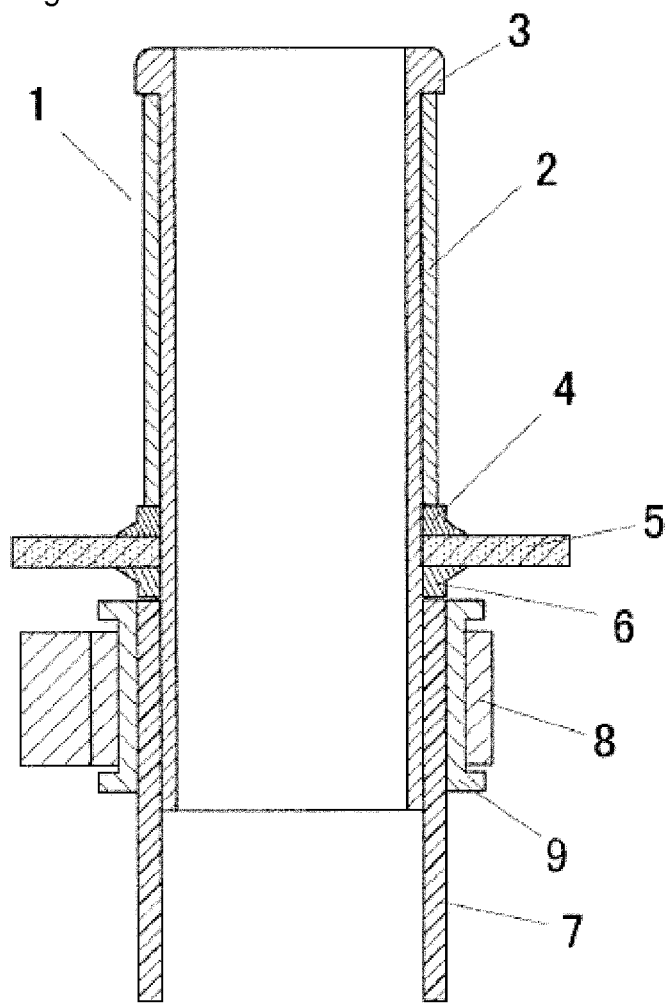
FIG. 5 is a cross-sectional diagram of the inflow cannula illustrated in FIGS. 2 to 4.

FIG. 5 is a cross-sectional diagram of the inflow cannula 1 illustrated in FIGS. 2 to 4. The inflow cannula 1 of the present invention can have the construction illustrated in FIG. 5, or can be embodied in another way, for example, as in the cross sectional diagrams of FIGS. 6 and 7.

Figure 6:
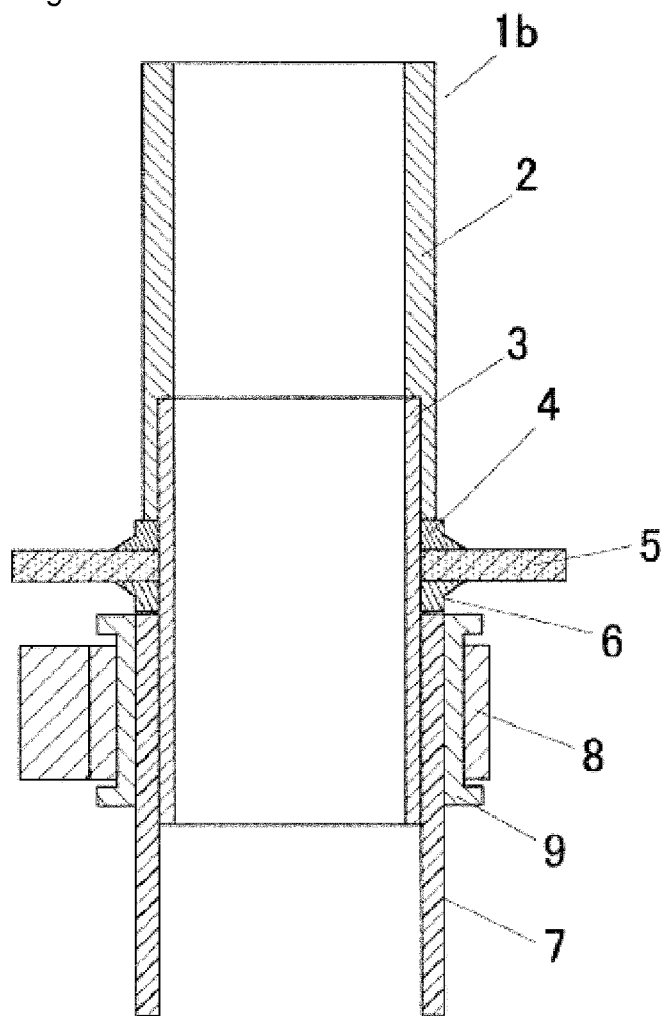
FIG. 6 illustrates a modification of the inflow cannula of the present invention, in which part of the inflow cannula has a two-layer structure.
Figure 7:
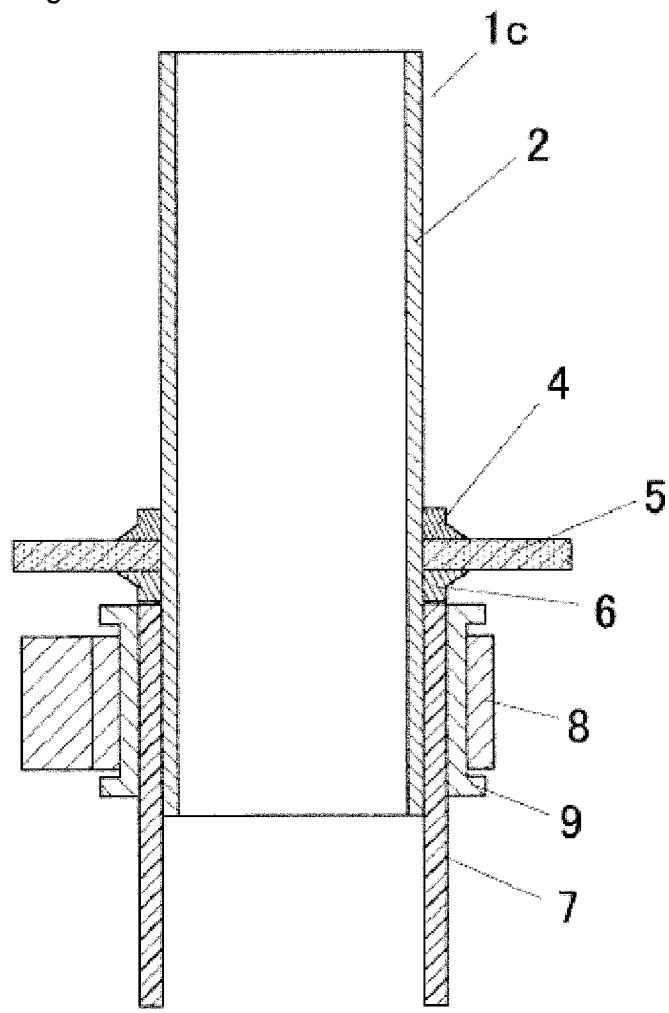
FIG. 7 illustrates a modification of the inflow cannula of the present invention, in which the inflow cannula has a one-layer structure.

In FIGS. 5 to 7, the reference numeral 1 (or 1b) denotes an inflow cannula with a non-porous support, and the reference numeral 1c an inflow cannula having no non-porous support. The reference numeral 2 denotes an inflow cannula main body comprising a porous structure, 3 denotes a support, 4 denotes a sleeve, 5 a cuff, 6 a cuff locking nut, 7 an artificial blood vessel, 8 an outer clamp, and 9 an inner clamp.

In the inflow cannula 1 of FIG. 5, the main body 2 is disposed in such a manner so as to cover the outer peripheral face of the support 3, except at the abutment portion 3b. In the inflow cannula 1b of FIG. 6, by contrast, there is used a short support 3 having no abutment portion, and most of the portion that is inserted into the heart (ventricle or atrium) constitutes a single-layer structure with the main body 2. In the inflow cannula 1b of FIG. 6, thrombi and/or endothelial cells are likely to become adhered, in an unstable manner, at the boundary between the support 3 and the main body 2, on the inner face of the inflow cannula 1b. With this in mind, the length of the support 3 is designed and adjusted in such a manner that this boundary lies at a position where blood flow is fast, so that it may be possible to prevent such unstable adhesion. The inflow cannula 1c of FIG. 7 does not use a support. Herein, the entire cannula has a single-layer structure comprising only the main body 2.

All the inflow cannulas 1, 1b, and 1c can be used as an inflow cannula for ventricular assist devices. However, in consideration of the mechanical strength of the inflow cannula as a whole, ease of insertion into the heart (ventricle or atrium), and prevention of excessive proliferation of cells at the leading end portion of the inflow cannula, it is preferable to use an inflow cannula having a two-layer structure, such as the inflow cannulas illustrated in FIGS. 2 to 5.

Blood flows abundantly on the inward side of the inflow cannula for ventricular assist devices, and is thus unlikely to pool at such portions. Hence, thrombi do not ordinarily form on the inward side of the inflow cannula, even when there is disposed a support having an ordinary smooth surface, as in the inflow cannulas of FIG. 5 and FIG. 6. When disposing a support having a smooth surface, as in FIG. 5 and FIG. 6, however, it is also possible, depending on the circumstances, to provide one further layer of the porous structure of the present invention on the radially inward side of the support.

If a porous structure is thus provided on the radially inward side of support, and if the inflow cannula is connected directly to the connector, the surface on the radially inward side of both the inflow cannula and the connector can be continuously covered with one porous structure by adjusting the length of the porous structure so as to allow covering up to the connector.

An example of a ventricular assist device being attached to the left ventricle will be explained next with reference to FIGS. 8 to 10. Herein, the ventricular assist device denotes an entire blood circulatory assist device comprising, for instance, a conduit assembly 10 to which an inflow cannula 1 is connected, a blood pump 11, a pump cable 12, a connector 13 and a battery 14.

Figure 8:
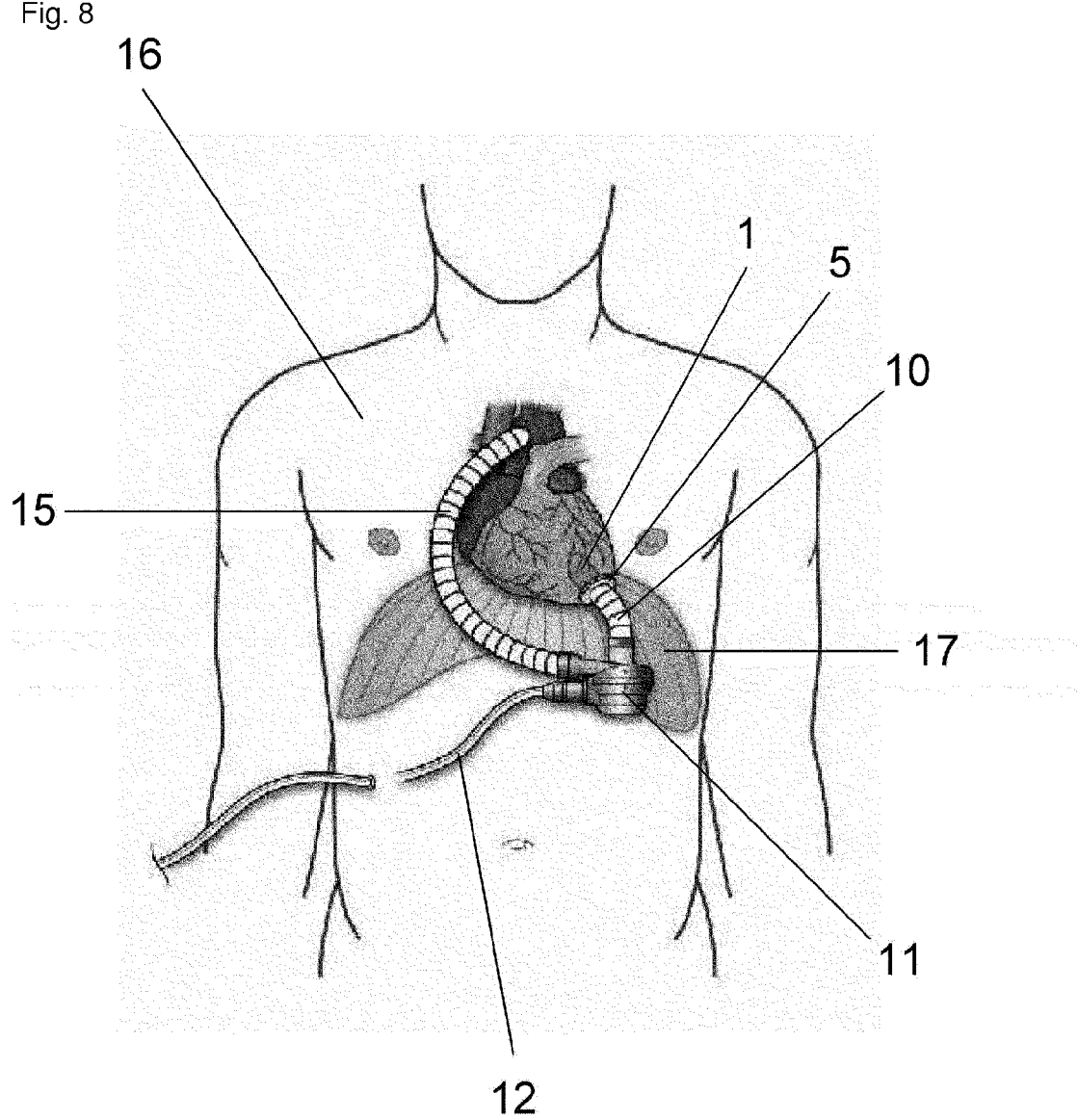
FIG. 8 is a front-view diagram illustrating the connection of a typical ventricular assist device to the heart of a patient.
Figure 9:
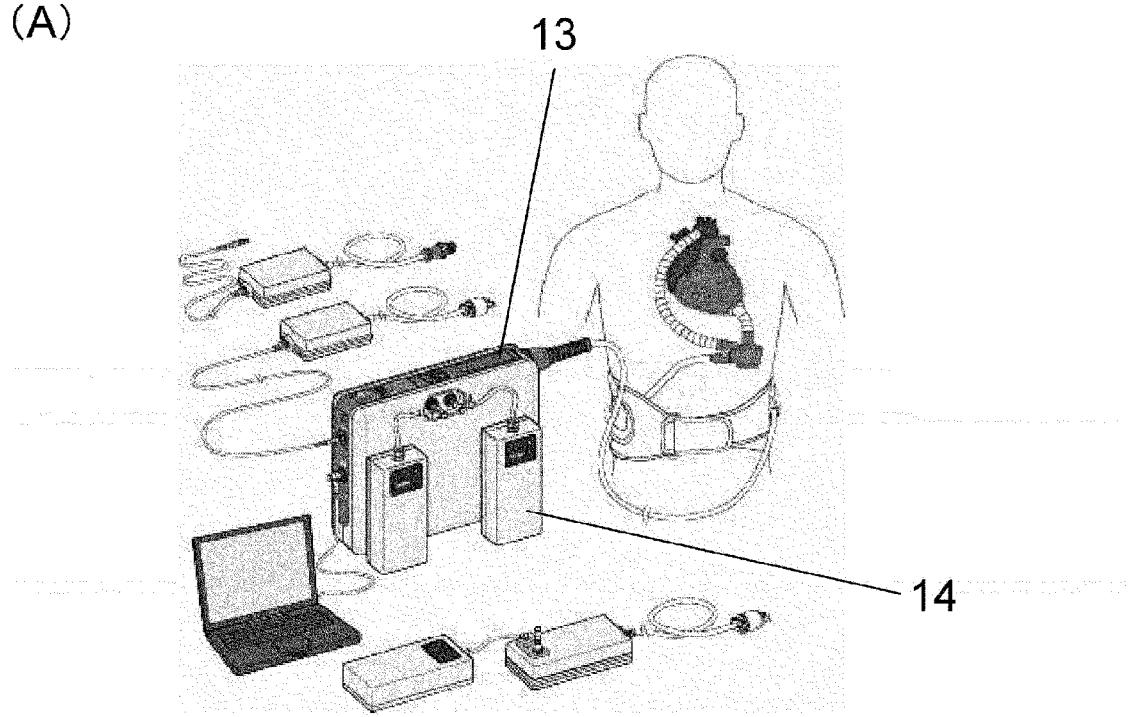
FIGS. 9A and B are front-view diagrams illustrating the connection of a typical ventricular assist device to the heart of a patient.
Figure 9:
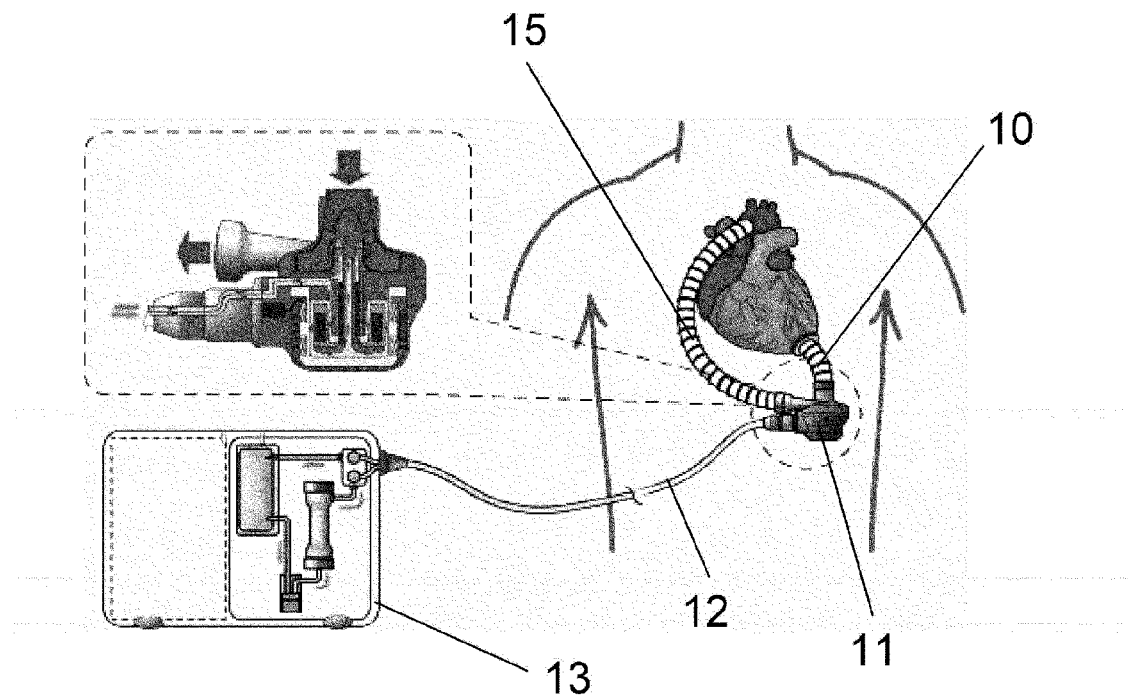

FIG. 8 is a diagram of a mounted ventricular assist device in one example. The figure illustrates a partial front view of a patient 16. The blood pump 11 of the ventricular assist device is surgically implanted on the thoracic cavity 17 of the patient. By way of the conduit assembly 10 provided with the inflow cannula 1, the ventricular assist device infuses blood from the left ventricle of the patient into the blood pump 11, and transports by an outflow graft 15 the blood from the blood pump 11 up to the thoracic ascending aorta of the patient.

The inflow cannula 1 is inserted into the left ventricle via ventricle wall of the heart, and is connected and fixed into the heart of the patient by sewing the cuff 5 placed at the distal part of the cannula onto the heart (In FIG. 8, the shape of the inflow cannula 1 is represented by a solid line at the position in which the cannula is inserted, although the inflow cannula cannot actually be seen from outside since it is inserted into the left ventricle.). The outflow graft 15 is connected to the ascending aorta, via the end of the outflow graft being sutured to the ascending aorta.

The pump cable 12 runs from the blood pump 11 through the body of the patient, and extends up to a space-saving controller 13, as illustrated in FIGS. 9A and 9B. The power source is the battery 14, which is connected to the controller 13.

Figure 10:
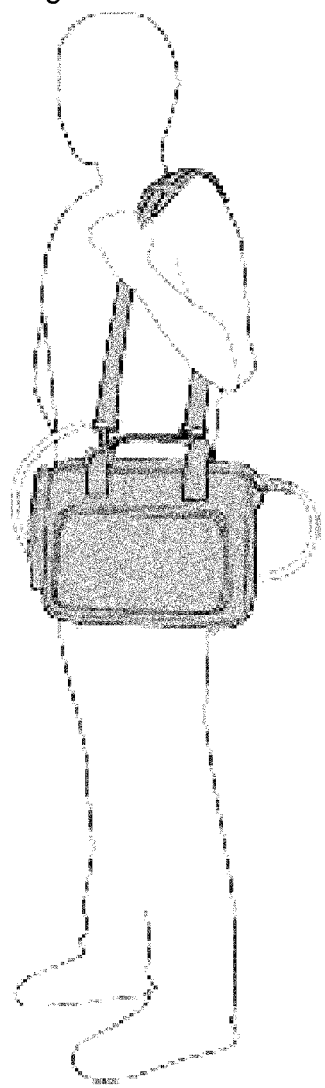
FIG. 10 shows that part of a ventricular assist device can be put into a shoulder bag.

For instance, the battery 14 and the controller 13, to which the pump cable 12 is connected, can be compactly stored in a shoulder bag which can be carried by the patient him or herself, as illustrated in FIG. 10.

Figure 11:
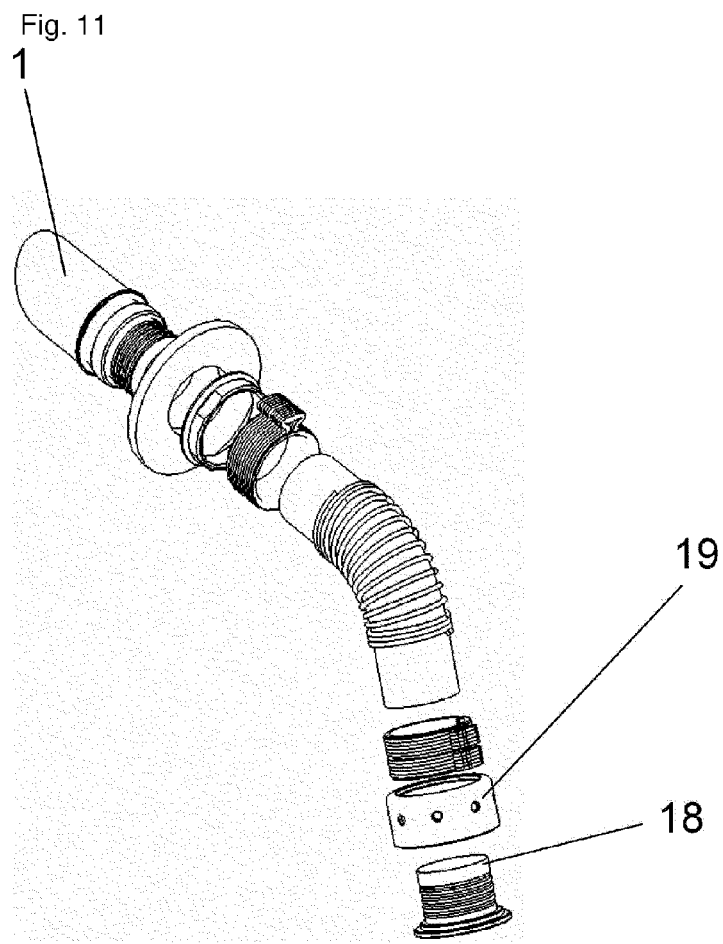
FIG. 11 is a perspective-view diagram of a connector comprising the structure of the present invention.
Figure 12:
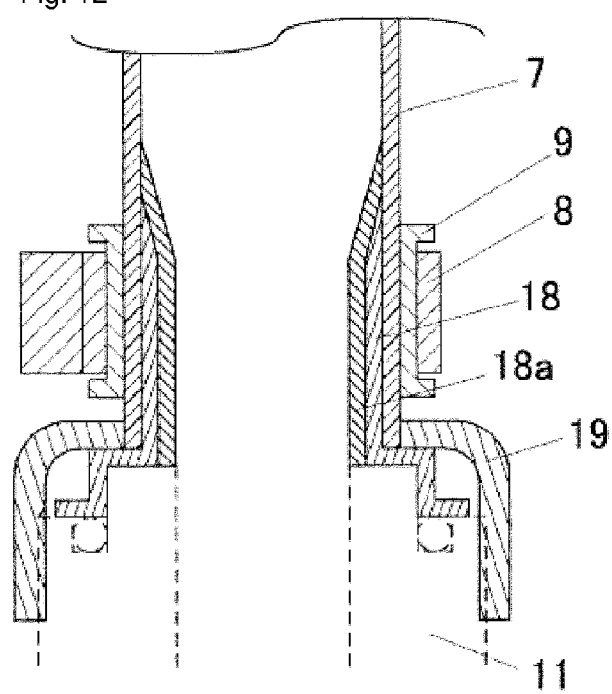
FIG. 12 is a cross-sectional diagram of a connector comprising the structure of the present invention.

As another example of the present invention, FIGS. 11 and 12 illustrate a connector having the porous structure of the present invention. FIG. 11 is a perspective-view diagram of the connector. FIG. 12 is a cross-sectional diagram of the connector. As illustrated in FIGS. 11 and 12, the connector 18 connects a blood pump and an artificial blood vessel, together with a holding ring 19. In FIG. 12, the reference numeral 18a denotes the porous structure of the present invention, closely fitted into the inside of the connector 18.

The present invention is explained in further detail next based on examples. Needless to say, however, the scope of the invention as defined in the appended claims is in no way meant to be limited to or by these examples.

EXAMPLES

Figure 13:
FIG. 13 illustrates a photograph of an inflow cannula of the present invention at autopsy, after 65 days of being implanted in vivo in an animal through insertion into the left ventricle, with tissue growth being observable on the outer peripheral face of the inflow cannula.

Two animal experiments were carried out using the inflow cannulas illustrated in FIGS. 2 to 5 (Two inflow cannulas were used on two respective calves (age 3 months, male, weight at implantation 86.5 kg; and age 3 months, male, weight at implantation 88.0 kg)). The calves were selectively sacrificed on POD 65 (post-operative day 65) and POD 63 (post-operative day 63). The implantation procedure was carried out through left thoracotomy with left ventricular pulsation. The above-described inflow cannula was inserted into the left ventricle, the blood pump was disposed in the thoracic cavity, and the outflow graft was joined to the descending aorta through end-to-side anastomosis. After implantation, the blood pump was driven stably at of 1864 to 1897 rpm and power consumption of 4.4 to 6.1 W. The health condition of the calves was good, and results of blood tests performed on them revealed no impaired renal function or the like, and no sings of infarction or the like caused by thrombus formation. Autopsy revealed that tissue had grown on the textured surface of the inflow cannula placed in the left ventricle (FIG. 13). As FIG. 13 also shows, growth of endothelial cells was discontinued at the abutment portion.

Figure 14:
FIG. 14 illustrates a photograph of a conventional inflow cannula having a smooth surface at autopsy, after 65 days of being implanted in vivo in an animal through insertion into the left ventricle, with substantial thrombus formation being observable on the outer peripheral face of the inflow cannula.

When using an inflow cannula having a conventional smooth surface, thrombi occurring at the base of the cannula are frequently observed (FIG. 14). In the present experiment, however, no such thrombi were observed. This phenomenon was observed for the two examples that were carried out. Pathological evaluation results showed that endothelial cells covered the textured surface. The present experiment suggests that endothelial cells in the inner wall of the left ventricle grow in a direction extending over the textured surface. In addition, it was proved that high antithrombogenicity was obtained due to endothelial cells having the function of controlling blood coagulation.

The inflow cannula manufactured in the examples retained a stable structure also when inserted into the left ventricle of the calves in the above-stated animal experiments, and damage, loosening of parts, or the like in the inflow cannula was not observed at autopsy.

The porous structure of the present invention possesses high mechanical strength and has numerous pores formed not only on the surface but also in the thickness direction, whereby it can exhibit a three-dimensional structure having voids of moderate size also in the thickness direction. This elicits as a result a high anchoring effect, and therefore, if the porous structure is placed at sites that neighbor on living tissue, stable adhesion of endothelial cells to the structure is achieved. The structure of the present invention can therefore be used for long-term indwelling at regions in the body where blood pools readily. Using the structure of the present invention allows preventing thrombi from detaching and/or entering into a blood vessel.

The porous structure of the present invention can be manufactured on its own, and can hence be manufactured independently as a device, instrument or the like having a textured surface. Furthermore, the porous structure may be manufactured separately, and be then disposed/fixed to a desired site of a blood-contacting surface of the ventricular assist device. In this case, the device, instrument or the like in which the porous structure is placed needs not be treated in a sintering furnace, and it is enough to dispose the structure, manufactured separately, on the site that is to be imparted a textured surface. Hence, the device, instrument or the like does not suffer deformation, chapping, loss of dimensional accuracy or the like, and it becomes thus possible to manufacture easily a device, instrument or the like having mixed smooth surface portions and textured surface portions.

REFERENCE SIGNS LIST

1: inflow cannula with non-porous support
1b: inflow cannula with non-porous support
1c: inflow cannula without non-porous support
2: main body
3: support
3a: support trunk portion
3b: support abutment portion in the form of a rim
3c: support screw portion
4: sleeve
5: cuff
6: cuff locking nut
7: artificial blood vessel
8: outer clamp
9: inner clamp
10: conduit assembly
11: blood pump
12: pump cable
13: controller
14: battery
15: outflow graft
16: patient
17: thoracic cavity
18: connector
18a: porous structure of the invention
19: holding ring

The invention claimed is:

1. An inflow cannula for ventricular assist devices, comprising a porous structure in part or in its entirety, for draining blood from the heart, said inflow cannula comprising the porous structure in a portion thereof which is configured to run through the ventricle wall or the atrium wall to be exposed into the heart and exposed to blood therein, wherein said porous structure is formed of one or more linear metallic elements and said porous structure has a plurality of pores which are configured to allow blood in the heart to flow into the porous structure and anchor thrombus generated by the inflowing blood congealing inside the porous structure; and wherein said porous structure is formed through intersection of one or more of the linear metallic elements, wherein said linear metallic elements form pores at the regions surrounded by lines that join mutually-adjacent intersection points on the surface of the porous structure.

2. The inflow cannula according to claim 1, wherein thrombus anchoring occurs in the porous structure.

3. The inflow cannula according to claim 2, wherein endothelial cells are adhered onto the anchored thrombi.

4. The inflow cannula according to claim 3, wherein the porous structure is covered by said endothelial cells.

5. The inflow cannula according to claim 1, further comprising a tubular non-porous support on its radially inward side.

6. The inflow cannula according to claim 5, wherein the non-porous support has an abutment portion in the form of a rim at one end.

7. A conduit assembly comprising an inflow cannula according to claim 1.

8. A ventricular assist device, having a conduit assembly according to claim 7.

9. The inflow cannula according to claim 1, wherein the porous structure is formed of one or more linear metallic elements spirally wound to form a hollow tubular body.

10. The inflow cannula according to claim 1, wherein the porous structure is formed of a nonwoven body made from one or more linear metallic elements.

11. The inflow cannula according to claim 1, wherein the material for the linear metallic elements is selected from stainless steel, pure titanium, or a titanium alloy.

12. The inflow cannula according to claim 1, wherein the porous structure comprises pores each having an opening surface area of $1.9 \times 10^{-5}$ mm$^2$ to 20 mm$^2$.

13. The inflow cannula according to claim 1, wherein an antithrombogenic coating is applied onto the surface of the one or more linear metallic elements.

14. A method for manufacturing an inflow cannula according to claim 1, the method comprising:
   (a) a step of spirally winding a linear metallic element around a tubular core from its one end toward the other end;
   (b) a step of spirally winding the same or a different linear metallic element on the spiral formed in step (a), so that the element intersects the linear metallic element spirally wound in step (a), thereby forming a tubular structure;
   (c) a step of sintering the tubular structure thus obtained from steps (a) and (b); and
   (d) a step of removing the core from the sintered tubular structure from step (c); and
   (e) optionally, a step of fitting a tubular non-porous support into the inside of the tubular structure from step (d), said tubular non-porous support having an outer diameter adapted in such a way that it enables the support to be fitted into the inside of the tubular structure and thereby to support the latter, and/or
   (f) optionally, a step of applying an antithrombogenic coating to the tubular structure from step (d) or to the entirety of the tubular structure fitted with the non-porous support from step (e).

15. A method for manufacturing an inflow cannula according to claim 1, further comprising:
   (a) a step of randomly charging one or more linear metallic elements into a formwork comprised of a base, and inner and outer walls concentrically disposed on the base, and fixing the elements, thereby obtaining a tubular structure in the form of a nonwoven; and
   (b) optionally, a step of fitting a tubular non-porous support into the inside of the tubular structure from step (a), said tubular non-porous support having an outer diameter adapted in such a way that it enables the support to be fitted into the inside of the tubular structure and thereby to support the latter, and/or
   (c) optionally, a step of applying an antithrombogenic coating to the tubular structure from step (a) or to the entirety of the tubular structure fitted with the non-porous support from step (b).

16. The inflow cannula according to claim 1, wherein a diameter of the linear metallic elements is 20 micrometer to 500 micrometer.

17. The inflow cannula according to claim 1, wherein a porosity of the porous structure is 5 to 90 vol %.

* * * * *